(12) United States Patent
Okamoto et al.

(10) Patent No.: US 10,780,127 B2
(45) Date of Patent: Sep. 22, 2020

(54) METHOD FOR PRODUCING FERMENTED MILK HAVING HIGH ANGIOTENSIN CONVERTING ENZYME INHIBITORY ACTIVITY AND METHOD FOR PRODUCING PHYSIOLOGICALLY ACTIVE PEPTIDE

(71) Applicants: NATIONAL UNIVERSITY CORPORATION TOTTORI UNIVERSITY, Tottori (JP); NATIONAL UNIVERSITY CORPORATION SHIMANE UNIVERSITY, Shimane (JP)

(72) Inventors: Kenji Okamoto, Tottori (JP); Toru Nabika, Izumo (JP)

(73) Assignees: NATIONAL UNIVERSITY CORPORATION TOTTORI UNIVERSITY, Tottori (JP); NATIONAL UNIVERSITY CORPORATION SHIMANE UNIVERSITY, Shimane (JP)

(*) Notice: Subject to any disclaimer, the term of this patent is extended or adjusted under 35 U.S.C. 154(b) by 0 days.

(21) Appl. No.: 16/311,827

(22) PCT Filed: Jun. 22, 2017

(86) PCT No.: PCT/JP2017/023100
§ 371 (c)(1),
(2) Date: Dec. 20, 2018

(87) PCT Pub. No.: WO2017/222029
PCT Pub. Date: Dec. 28, 2017

(65) Prior Publication Data
US 2019/0343884 A1 Nov. 14, 2019

(30) Foreign Application Priority Data
Jun. 23, 2016 (JP) .................. 2016-124765

(51) Int. Cl.
| | | |
|---|---|---|
| *A61K 35/20* | (2006.01) | |
| *A61P 9/12* | (2006.01) | |
| *A23C 9/13* | (2006.01) | |
| *A61K 36/06* | (2006.01) | |

(52) U.S. Cl.
CPC ............. *A61K 35/20* (2013.01); *A23C 9/13* (2013.01); *A61K 36/06* (2013.01); *A61P 9/12* (2018.01)

(58) Field of Classification Search
None
See application file for complete search history.

(56) References Cited

U.S. PATENT DOCUMENTS

5,854,029 A 12/1998 Yamamoto

FOREIGN PATENT DOCUMENTS

| | | |
|---|---|---|
| AU | 2011327288 | 5/2012 |
| CN | 104719471 | 6/2015 |
| JP | 59-44016 | 10/1984 |
| JP | 1-206970 | 8/1989 |
| JP | 2-283240 | 11/1990 |
| JP | 2003-48849 | 2/2003 |
| KR | 10-2006-0052760 | 5/2006 |
| WO | 2012/063826 | 5/2012 |

OTHER PUBLICATIONS

Li, S. and Shah, N., Journal of Dairy Science, 98:2949. (Year: 2015).*
International Search Report dated Sep. 19, 2017 in International Application No. PCT/JP2017/023100.
International Preliminary Report dated Dec. 27, 2018 in International Application No. PCT/JP2017/023100.
Yamamoto et al., "Purification and Characterization of an Antihypertensive Peptide from Yogurt-Like Fermented by Lactobacillus helveticus CPN4", J Dairy Sci, 1999, vol. 82, pp. 1388-1393.

* cited by examiner

*Primary Examiner* — Michael Barker
(74) *Attorney, Agent, or Firm* — Wenderoth, Lind & Ponack, L.L.P.

(57) ABSTRACT

The present invention provides fermented milk having a high angiotensin converting enzyme inhibition activity, a high hypotensive activity and/or a high stroke-preventing activity. The present invention also provides a method for producing fermented milk having a high angiotensin converting enzyme inhibition activity, a high hypotensive activity and/or a high stroke-preventing activity and a method for producing Tyr-Pro, each of which is characterized by comprising fermenting milk with a mushroom.

12 Claims, 6 Drawing Sheets

METHOD FOR PRODUCING FERMENTED MILK HAVING HIGH ANGIOTENSIN CONVERTING ENZYME INHIBITORY ACTIVITY AND METHOD FOR PRODUCING PHYSIOLOGICALLY ACTIVE PEPTIDE

FIELD

The present invention relates to a method for producing a food having a physiological activity, specifically, a method for producing fermented milk having an angiotensin converting enzyme inhibitory activity, a hypotensive activity, and/or a stroke prevention activity at high levels. Further, the present invention relates to a method for producing a physiologically active peptide, specifically, a method for producing Tyr-Pro. It should be noted that the present application is a patent application on the basis of the results of research entrusted by the nation or the like (a patent application pursuant to Article 19 of the Industrial Technology Enhancement Act with respect to "Science and technology research promotion program for agriculture, forestry, fisheries and food industry" conducted by the Ministry of Agriculture, Forestry and Fisheries in fiscal year 2016).

BACKGROUND

In recent years, the relationship between a food and health attracts increasingly more attentions, and it has been desired to develop a food that has a new and excellent physiological activity. Many studies have been conducted on physiological activities of foods, and foods having various physiological activities have been developed and sold on the market. In particular, many of physiological activities of fermented foods are worthy of attention. For example, fermented milk prepared using lactic acid bacteria with a proteolytic activity is known to have a hypotensive activity (e.g., see Patent literature 1).

As a substance showing the hypotensive activity in the fermented milk, peptides such as Ile-Pro-Pro, Val-Pro-Pro, and Tyr-Pro have been known. These peptides lower blood pressure by an angiotensin converting enzyme inhibitory activity. However, an inexpensive industrial production technology for these peptides has not been established yet and these peptides are expensive.

Thus, fermented milk having the angiotensin converting enzyme inhibitory activity, the hypotensive activity, and the like at further higher levels than the conventional fermented milk is demanded. Further, aforementioned peptides having the angiotensin converting enzyme inhibitory activity and the hypotensive activity are very expensive and thus there has been demanded a technology for producing these peptides in an inexpensive and simple manner.

CITATION LIST

Patent Literature

Patent Literature 1: International Patent Application Publication No. WO 2012/063826A1

SUMMARY

Technical Problem

A problem to be solved by the present invention was to obtain novel fermented milk having an angiotensin converting enzyme inhibitory activity, a hypotensive activity, and/or a stroke prevention activity at high levels. Further, another problem to be solved by the present invention was to produce a peptide having the angiotensin converting enzyme inhibitory activity in an inexpensive and simple manner.

Solution to Problem

As a result of earnest studies to solve the above problems, the present inventors have found that fermented milk obtained using a certain kind of mushroom has an angiotensin converting enzyme (ACE) inhibitory activity, a hypotensive activity, and/or a stroke prevention activity at very high levels and that the fermented milk thus obtained has a very large content of Tyr-Pro, thereby completing the present invention.

Specifically, the present invention relates to the followings:

(1) A method for producing fermented milk having an angiotensin converting enzyme inhibitory activity, a hypotensive activity, and/or a stroke prevention activity, which comprises fermenting milk using a mushroom.

(2) The method according to (1), wherein the mushroom is a mushroom belonging to Gloeophyllaceae family, Polyporaceae family, or Corticiaceae family.

(3) The method according to (2), wherein the mushroom is a mushroom belonging to *Neolentinus* genus, *Trametes* genus, or *Peniophora* genus.

(4) The method according to (3), wherein the mushroom is a mushroom belonging to *Neolentinus* genus or *Peniophora* genus.

(5) The method according to any of (1) to (4), wherein the milk is cow milk or skim milk.

(6) Fermented milk having an angiotensin converting enzyme inhibitory activity, a hypotensive activity, and/or a stroke prevention activity, which is obtained by the method according to any one of (1) to (5).

(7) A method for producing a food or drink having an angiotensin converting enzyme inhibitory activity, a hypotensive activity, and/or a stroke prevention activity, which comprises including the fermented milk according to (6) in the food or drink.

(8) A method for producing a pharmaceutical composition for angiotensin converting enzyme inhibitory, hypotension, and/or stroke prevention, which comprises including the fermented milk according to (6) in the composition.

(9) A method for producing Tyr-Pro, which comprises fermenting milk using a mushroom.

(10) The method according to (9), wherein the mushroom is a mushroom belonging to Gloeophyllaceae family, Polyporaceae family, or Corticiaceae family.

(11) The method according to (10), wherein the mushroom is a mushroom belonging to *Neolentinus* genus, *Trametes* genus, or *Peniophora* genus.

(12) The method according to (11), wherein the mushroom is a mushroom belonging to *Neolentinus* genus or *Peniophora* genus.

(13) The method according to any of (9) to (12), wherein the milk is cow milk or the skim milk.

Advantageous Effects of Invention

The fermented milk obtained by the present invention has an ACE inhibitory activity, a hypotensive activity, and/or a stroke prevention activity at very high levels, thus the fermented milk can be used to effectively perform a blood pressure control for a person who has high blood pressure, prevention of hypertension, prevention of stroke, and the like. Further, the fermented milk of the present invention has an anti-anxiety effect, a tranquilizing effect, an analgesic effect, a recovery effect for muscle fatigue, a taste exhibiting effect, and the like in addition to the ACE inhibitory effect, the hypotensive effect, and the stroke prevention effect. The fermented milk of the present invention, which is produced using an edible mushroom or a mushroom having no toxicity, has high safety. Further, according to the present invention, Tyr-Pro that has a physiological activity such as an ACE inhibitory effect, an anti-anxiety effect, and an analgesic effect can be inexpensively and simply produced from a material such as cow milk.

DESCRIPTION OF EMBODIMENTS

Figure 1:
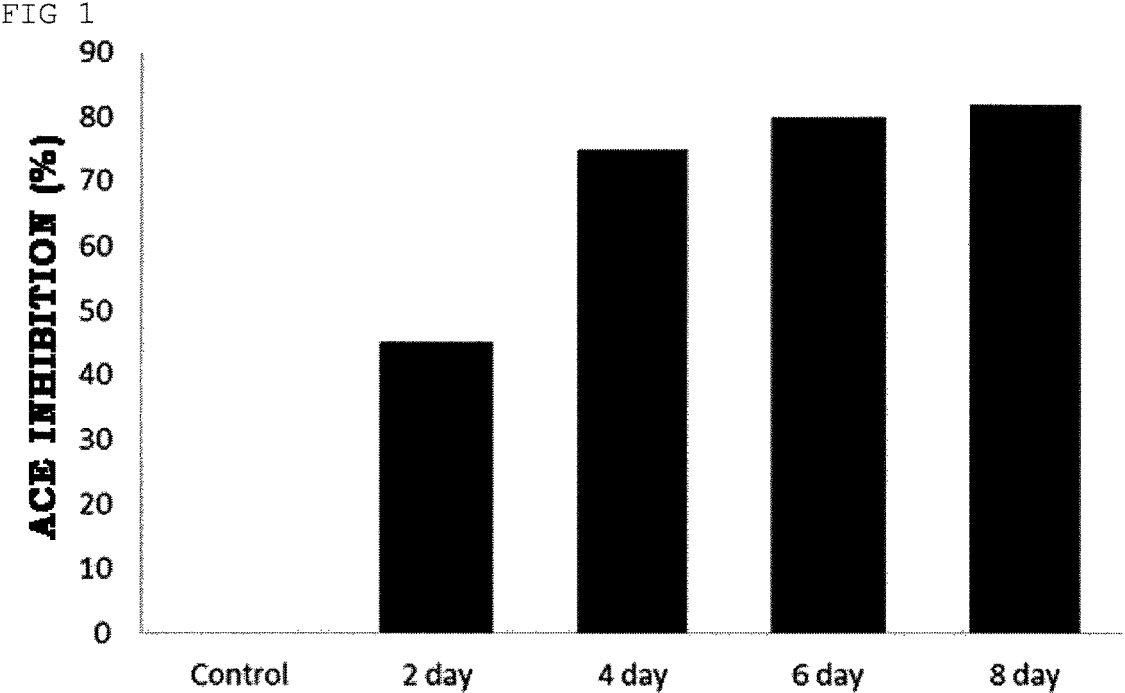
FIG. 1 is a graph showing a change over time in an ACE inhibitory activity of fermented milk obtained using *Neolentinus lepideus*.

In one embodiment, the present invention relates to a method for producing fermented milk, which comprises fermenting milk using a mushroom. The fermented milk obtained by the method of the present invention preferably has an ACE inhibitory activity, a hypotensive activity, and/or a stroke prevention activity.

In another embodiment, the present invention relates to fermented milk that has an ACE inhibitory activity, a hypotensive activity and/or a stroke prevention activity, the fermented milk being obtained by fermenting milk using a mushroom.

There is common technical knowledge that fermented milk is produced using lactic acid bacteria. Under such a circumstance, the present inventors attempted to produce fermented milk using a mushroom, and unexpectedly found that the fermented milk having an ACE inhibitory activity, a hypotensive activity, and/or a stroke prevention activity at very strong levels could be obtained. Further, the present inventors found that Tyr-Pro content in the fermented milk thus obtained is far higher than Tyr-Pro content in fermented milk obtained using lactic acid bacteria. The present invention was completed on the basis of these findings.

A mushroom is a fungus which forms a fruiting body having a size large enough to be observed by naked eyes. Many of mushrooms belong to Basidiomycota phylum or Ascomycota phylum. The mushroom used in the method for producing the fermented milk and the method for producing Tyr-Pro of the present invention is not particularly limited as long as it is used as a food or it has no toxicity. Examples of such a mushroom include, but are not limited to, *Pleurotus osteatus, Pleurotus cornucopiae* var. *citrinopileatus, Pleurotus pulmonarius, Pleurotus djamor, Pleurotus eryngii, Pleurotus nebrodensis, Pleurotus cystidiosus, Pleurotus abalonus, Neolentinus lepideus, Schizophyllum commune, Lentinula edodes, Lyophyllum decastes, Hypsizygus marmoreus, Lepista nuda, Lepista sordida, Trichoroma giantea, Armillaria* spp., *Panellus serotinus, Oudemansiella mucida, Mycena chlorophos, Flammulina velutipes, Leucopaxillus giganteus, Volvariella volvacea, Agaricus bisporus, Agaricus brazei, Coprinus comatus, Agrocybe cylindracea, Stropharia rugosoannulata, Stropharia rugosoannulata Farlow in Murrill f. lutea Hongo, Naematoloma sublateritium, Psilocybe* spp., *Pholiota nameko, Pholiota adiposa, Pholiota aurivella, Pholiota lubrica, Pholiota lenta, Sparassis crispa, Fistulina hepatica, Hericium ramosum, Hericium erinaceum, Climacodon septentrionalis, Mycoleptodonoides aitchisonii, Polyporus tuberaster, Favolus arcularius, Polyporus umbellatus, Meripilus giganteus, Grifola frondosa, Laetiporus sulphureus, Wolfiporia cocos, Ganoderma lucidum, Ganoderma neojaponicum, Elfvungia applanata, Inonotus oblizua, Phellius linteus, Tremella fuciformis, Tremella foliacea, Auricularia polytricha, Auricularia auricular*, and *Dictyophora indusiata*. In the present invention, the mushroom which can favorably ferment milk and generate an ACE inhibitory activity, a hypotensive activity, and/or a stroke prevention activity in the fermented milk, or the mushroom which can favorably ferment milk and produce a large amount of Tyr-Pro in the ferment milk is preferably used. Examples of the mushroom preferably used in the present invention include a mushroom in Gloeophyllaceae family, a mushroom in Corticiaceae family, a mushroom in Polyporaceae family, and the like.

Examples of the mushroom in Gloeophyllaceae family which can be used in the present invention include, but are not limited to, a mushroom in *Neolentinus* genus, for example, *Neolentinus lepideus*. *Neolentinus lepideus* is a brown putrefying fungus and a relatively large-sized mushroom grown on a stump or log of coniferous tree. *Neolentinus lepideus* is an edible mushroom which has an elastic texture and a lemonade aroma. Examples of the mushroom in the Polyporaceae family which can be used in the present invention include, but are not limited to, a mushroom in the *Trametes* genus, for example, *Trametes versicolor*. Examples of the mushroom in the Corticiaceae family which can be used in the present invention include, but are not limited to, a mushroom in the *Peniophora* genus, for example, *Peniophora* sp.

Examples of the mushroom preferably used in the present invention include, but are not limited to, a mushroom in the *Neolentinus* genus, the *Trametes* genus, or the *Peniophora* genus.

The mushroom which can be used in the present invention can be collected in a forest, a mountain field, an open field, or the like. The mushroom which can be used in the present invention can be obtained from an institution such as Fungus/Mushroom Resource and Research Center (FMRC) in affiliation with the Faculty of Agriculture, Tottori University; National Institute of Technology and Evaluation (NITE); and American Type Culture Collection (ATCC).

The milk used in the present invention is derived from a mammal. Examples of an animal species from which the milk is derived include, but are not particularly limited to, a cow, a goat, a sheep, a water buffalo, a yak, a camel, a donkey, a horse, a reindeer, a moose, and the like. Cow milk, which is massively produced and available at a relatively low price, is preferably used to produce a large amount of the fermented milk of the present invention. In the present specification, the term "milk" includes a processed product of the milk such as skim milk.

Fermentation of milk by a mushroom is performed by adding a hypha or a spore of the mushroom in milk or a liquid containing milk, and culturing it for a certain period of time. In fermentation of milk by a mushroom, a carbon source such as lactose, glucose, galactose, mannose, xylose, maltose, cellobiose, starch, and blackstrap molasses, and as a nitrogen source an organic nitrogen-containing product such as yeast extract, a casein hydrolysate, a whey protein hydrolysate, a soy protein hydrolysate, and corn steep liquor may be added to milk. An inorganic salt such as a phosphate salt, a sodium salt, a potassium salt, and a magnesium salt may be added to milk.

A fermentation temperature differs depending on factors such as a kind of mushroom, a kind of milk, a kind of additive to milk, and a fermentation time, however, it is normally 20° C. to 37° C., preferably 25° C. to 35° C., more preferably 28° C. to 33° C. The fermentation temperature can be appropriately changed. Fermentation is normally performed under an aerobic condition or a micro-aerobic condition. The micro-aerobic condition refers to a medium to low oxygen environment in which the mushroom can grow. Such a condition is known to a person skilled in the art and can be appropriately set. The fermentation can be performed by various known culture methods such as static culture, stirring culture, and shaking culture. A known culture vessel such as a flask, a jar, and a tank can be appropriately selected and used. During a fermentation process, pH may or may not be adjusted. The fermentation time also differs depending on factors such as a kind of mushroom, a kind of milk, a kind of additive to milk, and fermentation temperature, however, it is normally 1 day to 30 days, preferably 3 days to 21 days. The fermentation time can be appropriately changed. The fermentation time can be determined, for example, by measuring an ACE inhibitory activity, a production amount of the desired peptide, or the like in the fermented milk. Fermentation conditions can be determined by a person skilled in the art using ordinary knowledge or performing an ordinary test. Mushroom may be seeded in milk by adding a preliminarily prepared seed culture to the raw milk or adding the mushroom mycelium directly to the raw milk.

ACE inhibition in the present specification refers to the action of lowering the activity of the angiotensin converting enzyme. Specifically, it refers to the action of lowering the activity that catalyzes the conversion of angiotensin I to angiotensin II. ACE inhibition may be the action in vitro or in vivo. A measurement of ACE inhibitory activity can be performed by a known method (e.g., a method described in Cushman, D W., Cheung, H S. Spectrophotometric assay and properties of the angiotensin-converting enzyme of rabbit lung. Biochemical Pharmacology, 20: 1637-1648 (1971)). A kit for measuring ACE inhibitory activity is also commercially available.

The fermented milk of the present invention, which contains a large amount of Tyr-Pro and has a high ACE inhibitory activity, exhibits an excellent hypotensive effect. Hypotension in the present specification refers to the action of lowering blood pressure of a subject. A measurement of blood pressure can be performed by a known method. The fermented milk of the present invention may be used for a treatment and/or prevention of hypertension. Treatment of hypertension refers to the action of lowering the blood pressure of a subject to the normal blood pressure or the action of making the blood pressure of a subject closer to the normal blood pressure. Prevention of hypertension refers to the action of lowering possibility of onset of hypertension in a subject in the future.

The fermented milk of the present invention also has an excellent stroke prevention activity. Stroke includes cerebral hemorrhage, cerebral infarction, and subarachnoid hemorrhage. Prevention of stroke in the present specification refers to the action of lowering possibility of onset of stroke in a subject in the future.

The fermented milk of the present invention contains preferably 200 μg/ml or more, more preferably 300 μg/ml or more of Tyr-Pro produced by the fermentation.

Further, the fermented milk of the present invention is rich in a branched amino acid such as valine, leucine, and isoleucine, an aromatic amino acid such as phenylalanine, tryptophan, and tyrosine, and a taste exhibiting amino acid such as glutamic acid, thus, the fermented milk has an anti-anxiety effect, a tranquilizing effect, an analgesic effect, a recovery effect for muscle fatigue, a nutrient supplement effect, a taste exhibiting effect, and the like in addition to the ACE inhibitory effect, the hypotensive effect, and the stroke prevention effect.

The fermented milk of the present invention may be fermented milk itself which has been fermented by a mushroom, or fermented milk by a mushroom which has been subjected to a treatment or processing such as concentration, dilution and drying. These treatments and processing are known to a person skilled in the art and can be performed by known methods. Thus, a form of the fermented milk of the present invention may be determined without any particular limitation. The fermented milk of the present invention may be in a liquid form, a solid form, such as a powder, a granule, a flake, and a block, or a semi-solid form, such as gel, paste, and cream.

In still another embodiment, the present invention relates to a method for producing a food or drink that has an ACE inhibitory activity, a hypotensive activity, and/or a stroke prevention activity, which comprises including the fermented milk obtained by fermentation of milk using a mushroom, in a food, a food material, or a carrier or excipient.

In still another embodiment, the present invention relates to a food or drink that has an ACE inhibitory activity, a hypotensive activity, and/or a stroke prevention activity, wherein the food or drink contains the fermented milk obtained by fermentation of milk using a mushroom.

The food or drink of the present invention has an antianxiety effect, a tranquilizing effect, an analgesic effect, a recovery effect for muscle fatigue, a nutrient supplement effect, a taste exhibiting effect, and the like in addition to the ACE inhibitory effect, the hypotensive effect, and/or the stroke prevention effect.

The food containing the fermented milk obtained by fermentation of milk using the mushroom is not particularly limited, and may be any kind of food. The food material containing the fermented milk obtained by fermentation of milk using the mushroom is not particularly limited, and may be also any kind of food material. The food material is a material subjected to a treatment or processing for producing a food, and also includes a raw material for the food.

The food or drink of the present invention may be a liquid, a solid, such as a dried product, or a semi solid, such as paste. A method for producing the food or drink of the present invention in the solid, liquid, or semi-solid form is known. The fermented milk of the present invention may be served as it is as a food and drink. Alternatively, the fermented milk of the present invention may be included in a beverage, confectionery, a milk product such as cream and cheese, or the like to produce a food or drink. The fermented milk of the present invention may be also included in a food or drink other than the milk product to produce the food or drink.

The fermented milk and the food or drink of the present invention may be a supplement. A method for preparing the supplement is known and the supplement may be prepared using a carrier or excipient known in a pharmaceutical field. The supplement can be prepared as a liquid agent such as a drink agent or a concentrated liquid, a solid agent such as a tablet, a powder, a granule, or a drop, a semi solid agent such as cream, paste, or gel, or a capsule agent. The fermented milk having an ACE inhibitory activity, a hypotensive activity, and/or a stroke prevention activity at high levels, obtained using a mushroom, has not been known before. Thus, the food or drink containing such fermented milk is novel. The fermented milk of the present invention can be purified by a known method such as a chromatography method and fractionated into one or more fractions having the high ACE inhibitory activity to obtain a food or drink containing such fractions. Such a food or drink is also novel.

In still another embodiment, the present invention relates to a method for producing a pharmaceutical composition for angiotensin converting enzyme inhibition, hypotension, and/or stroke prevention, which comprises including the fermented milk obtained by fermentation of milk using a mushroom in a carrier or excipient. The carrier or excipient known in a pharmaceutical field can be used. The pharmaceutical composition of the present invention can be produced by a known process such as mixing, crushing, filling, and tableting. A known additive such as a coloring agent, a flavoring agent, and a sweetener may be used in the pharmaceutical composition of the present invention.

In still another embodiment, the present invention relates to a pharmaceutical composition for angiotensin converting enzyme inhibition, hypotension, and/or stroke prevention, which comprises the fermented milk obtained by fermentation of milk using a mushroom.

The pharmaceutical composition of the present invention can be used not only for ACE inhibition, hypotension, and stroke prevention, but also for anti-anxiety, tranquilization, analgesia, recovery from muscle fatigue, nutritional supplement, and the like.

The pharmaceutical composition of the present invention may have any dosage form without any particular limitation. The pharmaceutical composition may have a solid form such as a tablet, a drop, a granule, and a powder, a liquid form such as syrup, and a semi-solid form such as cream and paste, or the pharmaceutical composition may be prepared as a capsule agent. Methods for producing various dosage forms are known and may be applied to the pharmaceutical composition of the present invention. The pharmaceutical composition for ACE inhibition, hypotension, and/or stroke prevention may be produced by purifying the fermented milk of the present invention by a known method such as a chromatography method and using one or more fractions having ACE inhibitory activity, hypotensive activity, and/or stroke prevention activity at high levels.

In still another embodiment, the present invention relates to a method for producing Tyr-Pro, which comprises fermenting milk using a mushroom.

As described above, Tyr-Pro has an ACE inhibitory activity and thus has a hypotensive effect. It is also known that Tyr-Pro has an anti-anxiety effect and is important for an analgesic activity.

The milk used for the method for producing Tyr-Pro of the present invention is as described above.

The mushroom used for the method for producing Tyr-Pro of the present invention is also as described above. In addition to that, the mushroom having toxicity can be also used in a case where Tyr-Pro can be separated from a toxic substance by a subsequent operation. The mushroom preferably used in the method for producing Tyr-Pro of the present invention is a mushroom in Gloeophyllaceae family, a mushroom in Polyporaceae family, a mushroom in Corticiaceae family, or the like. These mushrooms have been already described above. Examples of the mushroom more preferably used in the method for producing Tyr-Pro of the present invention include, but are not limited to, a mushroom in *Neolentinus* genus, in *Trametes* genus, or in *Peniophora* genus.

Conditions of milk fermentation in the method for producing Tyr-Pro of the present invention can be also appropriately determined by a person skilled in the art. Various conditions, such as a kind of mushroom, a kind and concentration of milk, a fermentation temperature, a fermentation time, a fermentation pH, an aeration/stirring condition, and a culture vessel, can be selected by a person skilled in the art to increase the production amount of Tyr-Pro.

Tyr-Pro in the fermented milk can be quantified by a known method such as HPLC. Tyr-Pro generated in the fermented milk can be subjected to solid-liquid separation by a method such as centrifugal separation and membrane separation and purified by a known separation and purification method such as ion-exchange chromatography, gel filtration, and hydrophobic chromatography to obtain a purity in accordance with the purpose of use.

The present invention will be described below in a more detailed and specific manner by way of Examples. It should be noted however that the present invention is not limited by the following Examples. [Example 1]

Example 1. Production of Fermented Milk Having ACE Inhibitory Activity Using a Mushroom (1) Pre-culture of *Neolentinus lepideus*

A hypha grown on an MYG medium (1.0% malt extract broth, 0.4% yeast extract, 0.4% glucose, 1.5% agar) was cut into a 5 mm$^2$ size, seeded into a 50 ml MYG liquid medium for pre-culture (1.0% malt extract broth, 0.4% yeast extract, 0.4% glucose), and cultured at 28° C. for 7 to 9 days. Then, the cultured mycelia thus grown were separated by filtration under an aseptic condition and used for the production of the fermented milk. *Neolentinus lepideus* used in the test was deposited in National Institute of Technology and Evaluation Patent Microorganisms Depositary, #122, 2-5-8 Kazusakamatari, Kisarazu-shi, Chiba 292-0818, Japan, under a receipt number NITE AP-02283 on Jun. 8, 2016 on the basis of the Budapest Treaty on the International Recognition of the Deposit of Microorganisms for the Purposes of Patent Procedure. This *Neolentinus lepideus* strain was transferred to international deposit by the same institution under a deposit number NITE BP-02283 on Jun. 9, 2017. This *Neolentinus lepideus* strain was used for the following tests.

(2) Production of Fermented Milk by *Neolentinus Lepideus* and ACE Inhibitory Activity The mycelia obtained by pre-culture was seeded in an autoclaved cow milk medium and cultured at 28° C. under a micro-aerobic condition. A part of the culture was collected as a sample on a daily basis and subjected to centrifugal separation (4° C., 15,000 rpm, 10 min). The sample obtained by filtering the supernatant was processed using ACE Kit-WST (manufactured by DOJINDO LABORATORIES). The result is shown in FIG. 1. The ACE inhibitory activity increased on a daily basis, and the ACE activity was inhibited by about 70% or more on the fourth day of fermentation and the ACE activity was inhibited by about 80% on the sixth day or later of fermentation.

(3) Comparison of ACE inhibitory activity between fermented milk obtained using *Neolentinus lepideus* and commercially available food for specified health uses.

Figure 2:
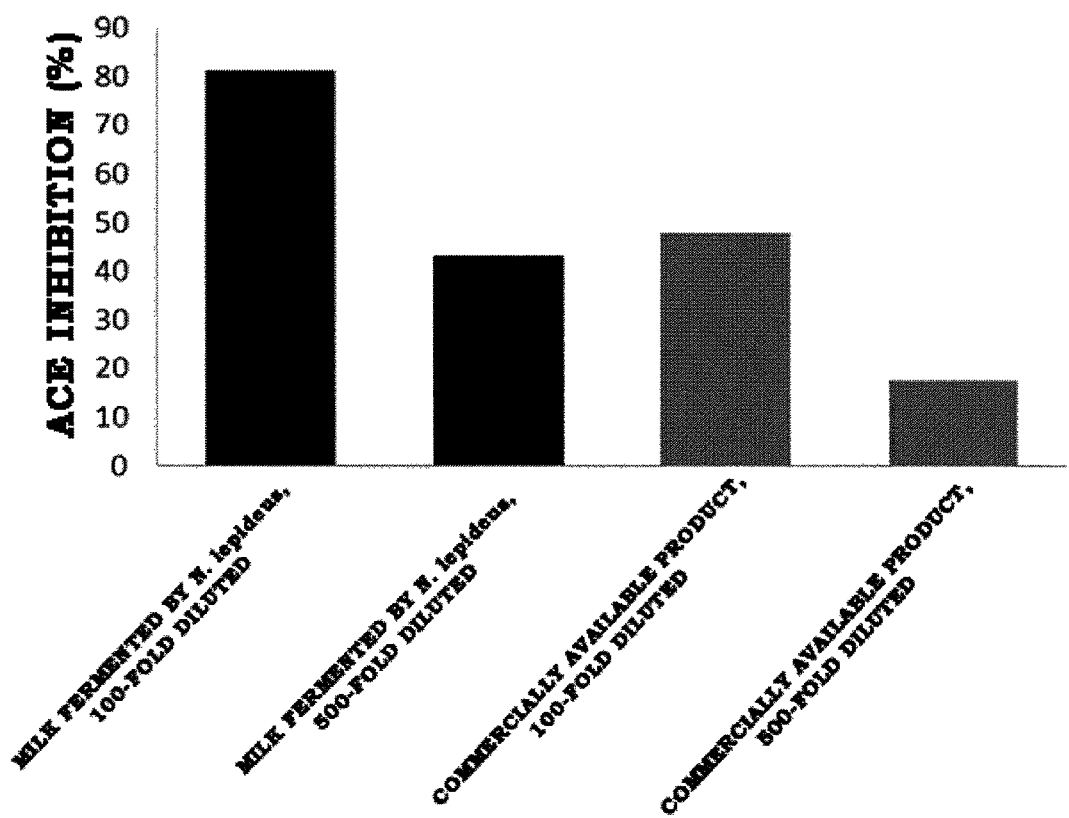
FIG. 2 is a graph showing a comparison of an ACE inhibitory activity between the fermented milk obtained using *Neolentinus lepideus* and a commercially available product.

The ACE inhibitory activity was compared in the same manner as described above between the fermented milk obtained by performing fermentation for 6 days using *Neolentinus lepideus* and a commercially available food for specified health uses (a milky beverage produced from cow milk through the action of lactic acid bacteria, which is said to be suitable for a person having relatively high blood pressure). The fermented milk of the present invention and the commercially available food for specified health uses (containing lactotripeptides VPP and IPP) were each diluted 100 fold and 500 fold to prepare samples. The result of testing the ACE inhibitory activity is shown in FIG. 2. The 100-fold dilution of the fermented milk of the present invention had almost twice the ACE inhibitory activity compared with the 100-fold dilution of the commercially available food for specified health uses. The 500-fold dilution of the fermented milk of the present invention had the two times or higher ACE inhibitory activity compared with the 500-fold dilution of the commercially available food for specified health uses. The fermented milk of the present invention showed the ACE inhibitory activity even after 1,000-fold dilution, while the commercially available food for specified health uses hardly showed the ACE inhibitory activity after 1,000-fold dilution. From these results, it was found that the fermented milk of the present invention had the higher ACE inhibitory activity compared with the commercially available food for specified health uses.

Figure 3:
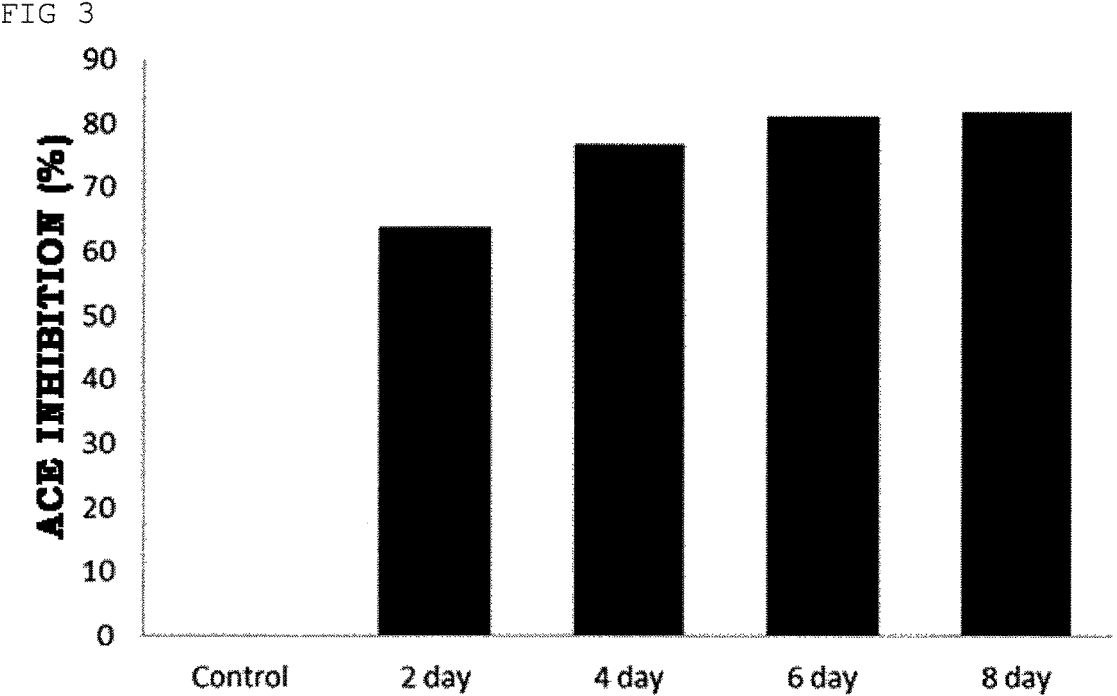
FIG. 3 is a graph showing a change over time in an ACE inhibitory activity of the fermented milk obtained using *Peniophora* sp.

(4) Production of Fermented Milk by *Peniophora* sp. and ACE Inhibitory Activity The fermented milk was produced using *Peniophora* sp. and the ACE inhibitory activity of the fermented milk was tested in the same manner as in above (2). The result is shown in FIG. 3. The ACE inhibitory activity increased on a daily basis, and the ACE activity was inhibited by about 70% or more on the fourth day of fermentation and the ACE activity was inhibited by about 80% on the sixth day or later of fermentation. *Peniophora* sp. used in the test was deposited in National Institute of Technology and Evaluation Patent Microorganisms Depositary, #122, 2-5-8 Kazusakamatari, Kisarazu-shi, Chiba 292-0818, Japan, under a receipt number NITE AP-02284 on Jun. 8, 2016 based on the Budapest Treaty on the International Recognition of the Deposit of Microorganisms for the Purposes of Patent Procedure. This *Peniophora* sp. strain was transferred to international deposit by the same institution under a deposit number NITE BP-02284 on Jun. 9, 2017. This *Peniophora* sp. strain was used for the following tests.

Figure 4:
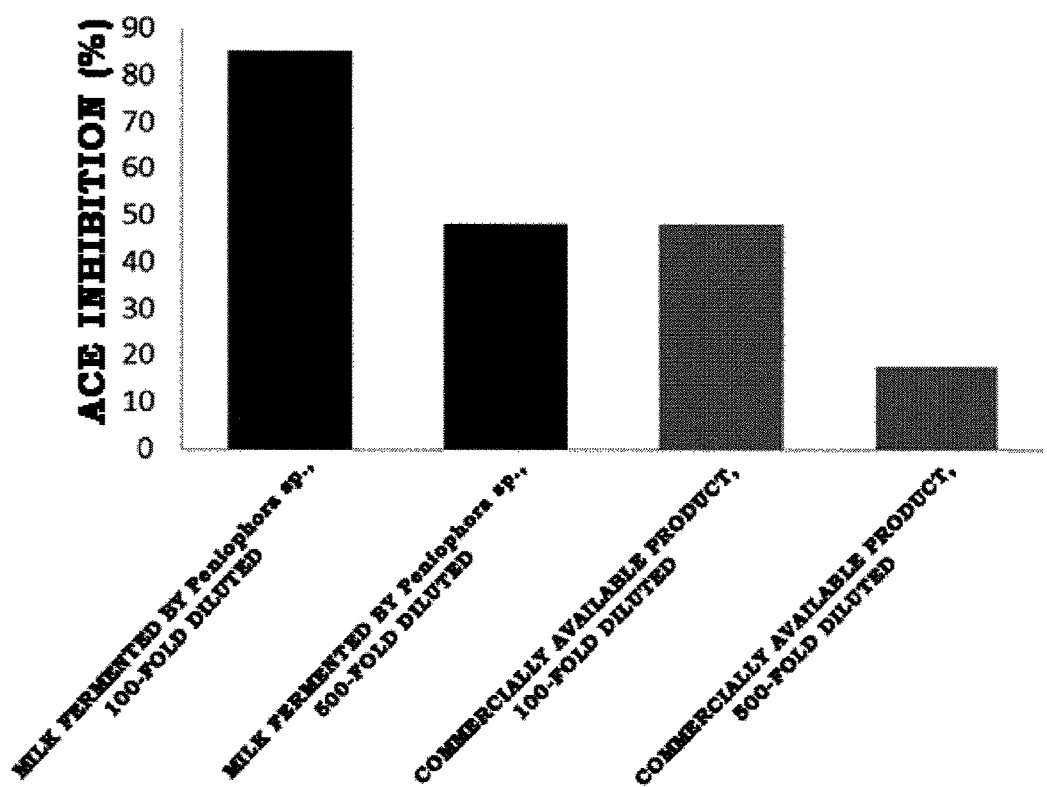
FIG. 4 is a graph showing a comparison of an ACE inhibitory activity between the fermented milk obtained using *Peniophora* sp. and a commercially available product.

(5) Comparison of ACE inhibitory activity between fermented milk obtained using Peniophora sp. and commercially available food for specified health uses The ACE inhibitory activity was compared in the same manner as in above (3) between the fermented milk obtained by performing fermentation for 6 days using Peniophora sp. and a commercially available food for specified health uses (a milky beverage produced from cow milk through the action of lactic acid bacteria, which is said to be suitable for a person having relatively high blood pressure). The result is shown in FIG. 4. The 100-fold dilution of the fermented milk of the present invention had almost twice the ACE inhibitory activity compared with the 100-fold dilution of the commercially available food for specified health uses. The 500-fold dilution of the fermented milk of the present invention had the two times or higher ACE inhibitory activity compared with the 500-fold dilution of the commercially available food for specified health uses. The fermented milk of the present invention showed the ACE inhibitory activity even after 1,000-fold dilution, while the commercially available food for specified health uses hardly showed the ACE inhibitory activity after 1,000-fold dilution. From these results, it was found that the fermented milk of the present invention had the higher ACE inhibitory activity compared with the commercially available food for specified health uses.

(6) Hypotensive Effect of Fermented Milk Obtained Using *Neolentinus lepideus* on Stroke-Prone Spontaneously Hypertensive Rat (SHRSP)

Ten male SHRSPs aged 10 or 8 weeks were divided into 2 groups, and the rats in a control group were freely allowed to ingest distilled water and the rats in a test group were freely allowed to ingest the 3-fold dilution of the fermented milk. The blood pressure was measured once a week by a tail-cuff method. At the same time, the amount of water drunk, the amount of feed taken, and body weight were measured.

Figure 5:
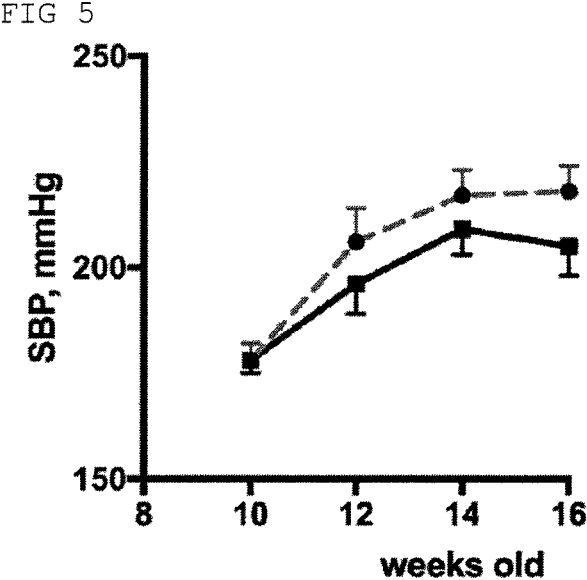
FIG. 5 is a graph showing a result of examination of a hypotensive effect of the fermented milk obtained using *Neolentinus lepideus* on a stroke-prone spontaneously hypertensive rat (SHRSP). A solid line shows systolic blood pressure in a group to which the milk fermented by *Neolentinus lepideus* was administered, while a broken line shows systolic blood pressure in a control group.

The result is shown in FIG. 5. A significant difference (p=0.027) in the systolic blood pressure was observed between the fermented milk group and the control group from around the second week after start drinking. The hypotensive effect of the fermented milk obtained using *Neolentinus lepideus* on SHRSPs was confirmed by this result.

(7) Stroke Prevention Effect of Fermented Milk Obtained Using *Neolentinus lepideus* on Stroke-Prone Spontaneously Hypertensive Rat (SHRSP Rat)

Twelve male SHRSPs aged 12 weeks were divided into 2 groups, and the rats in a control group were freely allowed to ingest 1% saline water and the rats in a test group were freely allowed to ingest 1% saline water in which a 3-fold dilution of the fermented milk was added. The number of days until the onset of stroke was measured. The onset of stroke was judged by paralysis, spasticity, akinesia, rapid weight loss, or the like, and cerebral infarction and cerebral hemorrhage were confirmed by MRI.

Figure 6:
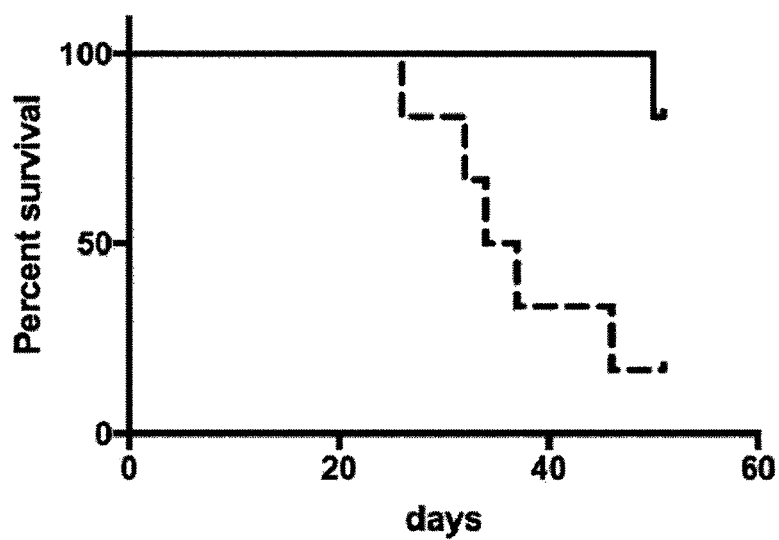
FIG. 6 is a graph showing a result of examination of a stroke prevention effect of the fermented milk obtained using *Neolentinus lepideus* on the stroke-prone spontaneously hypertensive rat (SHRSP). A solid line shows a survival rate in a group to which the milk fermented by *Neolentinus lepideus* containing 1% saline was administered, while a broken line shows a survival rate in a control group.

The result is shown in FIG. 6. In the fermented milk group, only one out of six rats died due to the onset of stroke, while, in the control group, five out of six rats died due to the onset of stroke. There was a significant difference ($p=0.01$) between them in accordance with the log-rank test. The stroke prevention effect of the fermented milk obtained using *Neolentinus lepideus* on SHRSPs was confirmed by this result.

Example 2

Example 2. Production of Tyr-Pro (YP) by Fermentation of Milk Using a Mushroom (1) Identification of YP in Fermented Milk In the same manner as in (1) of Example 1, the *Neolentinus lepideus* mycelia obtained by pre-culture were seeded in a liquid containing 9% (w/w) skim milk and cultured at 28° C. under a micro-aerobic condition. A part of the culture was collected as a sample on a daily basis and subjected to centrifugal separation (15,000 rpm, 10 min). The supernatant was filtered by a 0.22 μm filter (Millex-GP manufactured by Millipore Corp.) to obtain a sample. The sample was fractionated with reversed-phase HPLC (Prominence model manufactured by Shimadzu Corp.) using a Cadenza CD-C18 column (a column size of 4.6 mm×150 mm, manufactured by Imtakt Corp.). Elusion was performed by first applying a solution A (0.1% trifluoroacetic acid-H2O) for 5 minutes at a flow rate of 0.6 ml/min and a column temperature of 28° C. and then setting a linear concentration gradient from the solution A to a 20% solution B (0.1% trifluoroacetic acid-acetonitrile) after 100 minutes. Peptides were detected by 215 nm ultraviolet light.

A peak fraction at the retention time of 52 minutes, in which the activity tended to increase in accordance with the progress of fermentation, was collected and subjected again to the reversed-phase HPLC under the above conditions. The ACE inhibitory activity of this peak fraction was examined using a kit, ACE Kit-WST, manufactured by DOJINDO LABORATORIES. As a result, this fraction had an ACE inhibitory rate of 40 to 55%, which was higher than that of other fractions.

Figure 7:
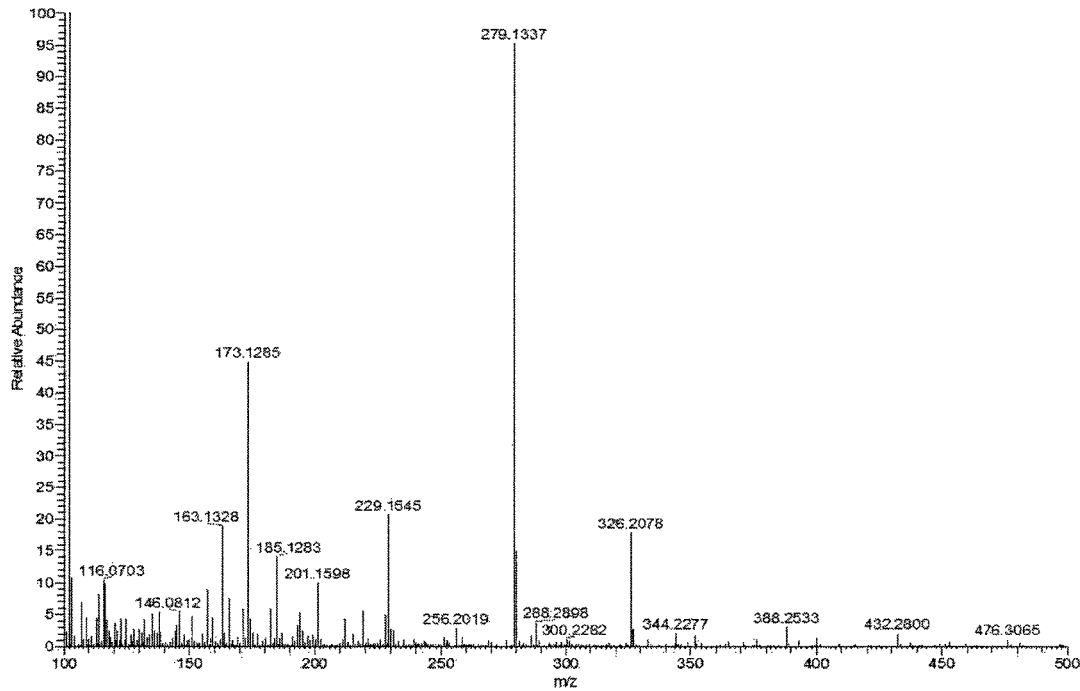
FIG. 7 is a chart of electrospray ionization mass spectrometry analysis (ESI-MS) showing a result of identification of Tyr-Pro in the fermented milk obtained using *Neolentinus lepideus*.

The peak fraction described above was subjected to peptide sequence using a protein primary structure analyzer (PPSQ-31A manufactured by Shimadzu Corp.) to obtain a result identifying Tyr-Pro. Further, the peak fraction described above was subjected to electrospray ionization mass spectrometry (ESI-MS) in a positive ion mode using a mass spectrometer (Exactive™ Plus Orbitrap manufactured by Thermo Fisher Scientific). The result is shown in FIG. 7. A signal m/z 279.1339[M+H]$^+$ corresponding to a molecular weight of 278.31 of Tyr-Pro (YP) was detected to demonstrate that the peak was caused by the dipeptide YP.

(2) Screening of YP Producing Fungus

Figure 8:
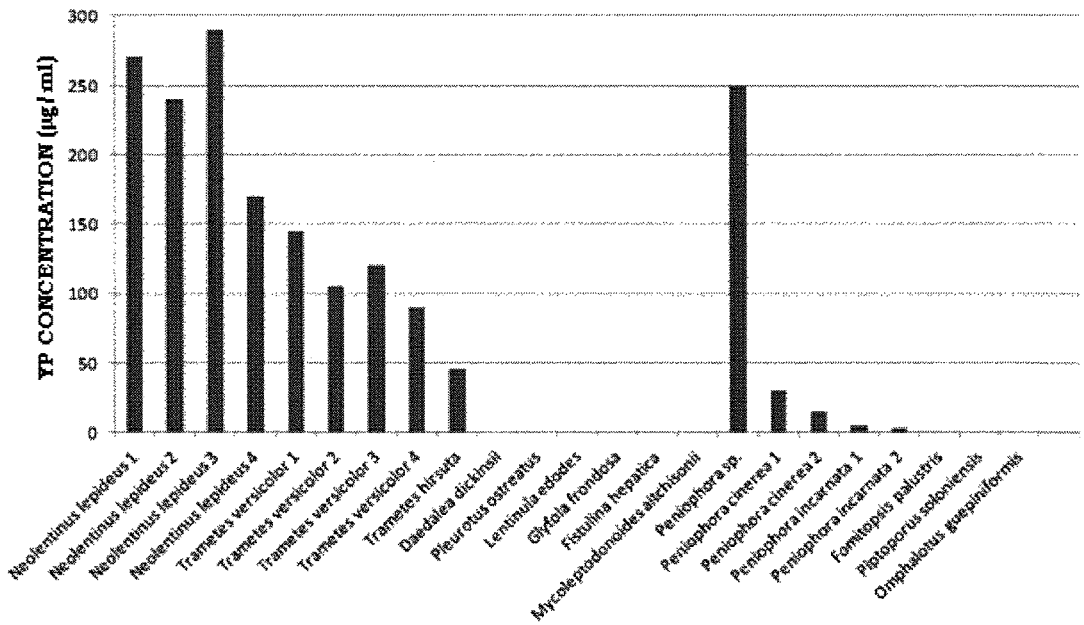
FIG. 8 is a graph showing a screening result of Tyr-Pro producing fungi.

The mycelia derived from 23 wild mushrooms were obtained by performing pre-culture in the same manner as in (1) of Example 1 and cultured in a liquid containing 9% (w/w) skim milk at 28° C. under a micro-aerobic condition for 6 days. The production amount of YP in the fermented milk was measured by the reversed-phase HPLC. YP in the fermented milk was measured on the basis of a calibration curve created using chemical synthetic products manufactured by BEX Co., Ltd. as a reference. The result is shown in FIG. 8. All four *Neolentinus lepideus* strains (*Neolentinus lepideus* 1-4) thus tested produced YP. Of these, *Neolentinus lepideus* 1-3 produced a large amount of YP, while *Neolentinus lepideus* 4 produced a relatively large amount of YP. All five *Trametes* strains (*Trametes versicolor* 1-4 and *Trametes hirsuta*) thus tested produced YP. Of these, *Trametes versicolor* 1-4 produced a relatively large amount of YP. All five *Peniophora* strains (*Peniophora* sp., *Peniophora cinerea* 1-2, and *Peniophora* incarnate 1-2) thus tested produced YP. Of these, *Peniophora* sp. produced a large amount of YP.

(3) Change Over Time in YP Production Amount by *Neolentinus lepideus*

Figure 9:
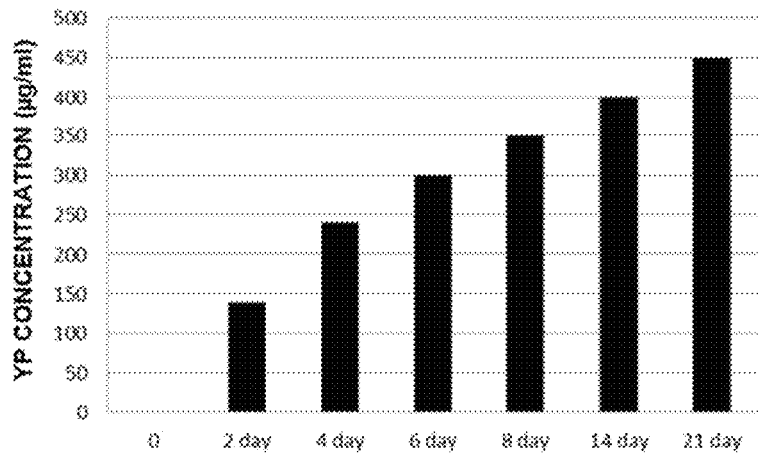
FIG. 9 is a graph showing a change over time in Tyr-Pro concentration in the fermented milk obtained using *Neolentinus lepideus*.

In the same manner as in Example 1, fermentation was performed in a liquid containing 9% (w/w) skim milk using *Neolentinus lepideus* and a sample was taken with time to measure the production amount of YP using HPLC. The result is shown in FIG. 9. The production amount of YP increased over time, became 200 μg/ml or more on fourth day or later, and reached 450 μg/ml on twenty first day. The IC$_{50}$ value of YP for ACE is reported to be 720 μM, which corresponds to 200 μg/ml. According to Patent literature 1, the production amount of YP by lactic acid bacteria (*Lactobacillus helveticus*) was about 70 μg/ml at maximum.

(4) Change Over Time in YP Production Amount by *Peniophora* sp.

Figure 10:
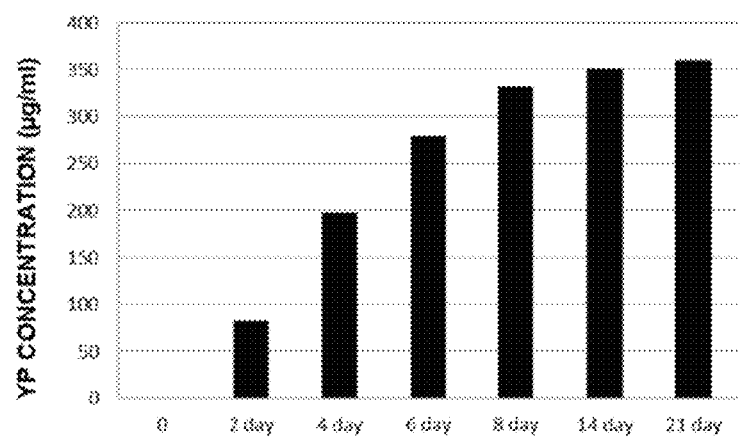
FIG. 10 is a graph showing a change over time in Tyr-Pro concentration in the fermented milk obtained using *Peniophora* sp.

Fermentation was performed in the same manner as in above (3) except that *Peniophora* sp. was used as a fungus strain. The production amount of YP was measured using HPLC. The result is shown in FIG. 10. The production amount of YP increased over time, became about 200 μg/ml on fourth day, and reached 350 μg/ml or more on twenty first day.

Figure 11:
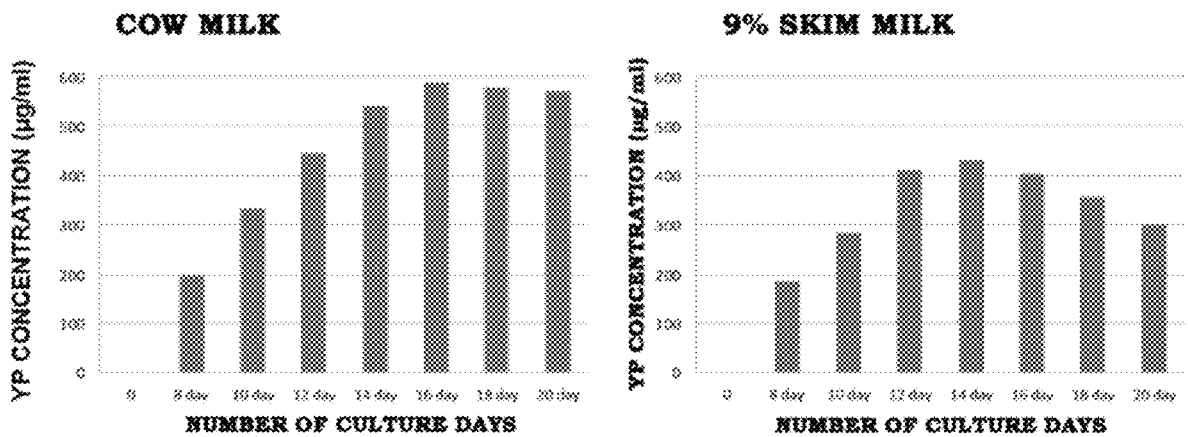
FIG. 11 is a graph showing a change over time in Tyr-Pro concentration in the fermented milk obtained by directly seeding a mycelium of *Peniophora* sp. in a raw material without performing pre-culture. A left panel shows Tyr-Pro concentration in a case where cow milk is used as a raw material, while a right panel shows Tyr-Pro concentration in a case where skim milk is used as a raw material.

*Peniophora* sp. was used as a fungus strain. Different from the above test, culture was performed by adding the mycelium directly into the cow milk or skim milk (9%) without performing pre-culture. In the cow milk, a maximum of 590 μg/ml of YP was obtained on sixteenth day of culture (a left panel in FIG. 11), while, in the skim milk, a maximum of 430 μg/ml of YP was obtained on fourteenth day of culture (a right panel in FIG. 11).

From these results, it was found that a large amount of YP could be obtained by fermenting milk using a mushroom. YP is known to have an ACE inhibitory effect, a hypotensive effect, an anti-anxiety effect, an analgesic effect, and the like. Thus, the fermented milk of the present invention containing a large amount of YP has such effects.

Example 3

Example 3: Amino Acid Analysis of Mushroom Fermented Milk (1) Amino Acid Analysis of Milk Fermented by *Neolentinus lepideus*

Figure 12:
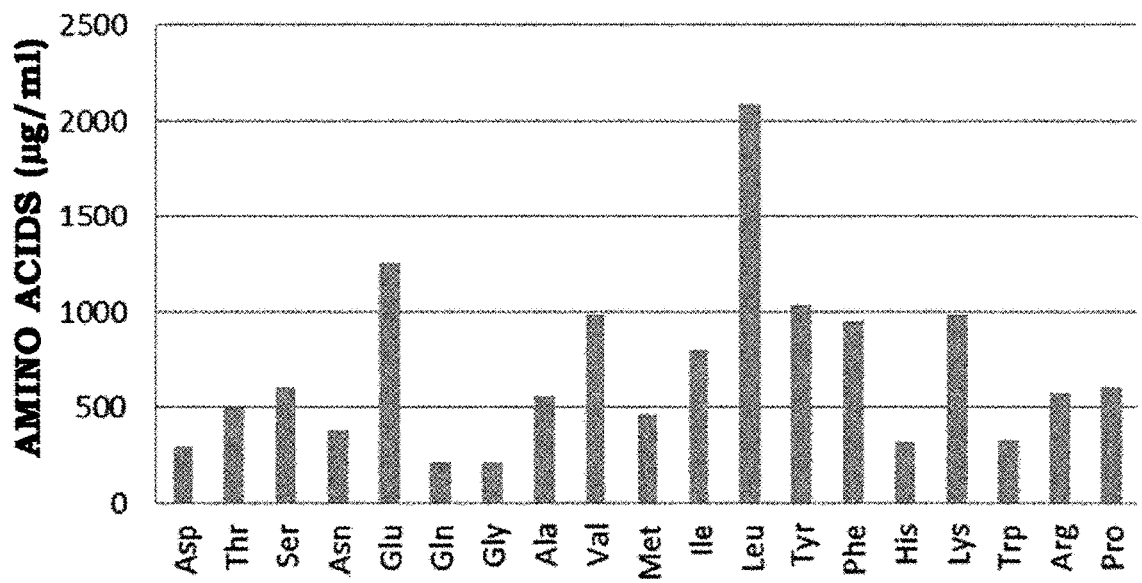
FIG. 12 is a graph showing a result of amino acid analysis of the fermented milk obtained using *Neolentinus lepideus*.

*Neolentinus lepideus* was stationarily cultured in a liquid containing 9% (w/w) skim milk at 30° C. for 8 days. The amount of the produced amino acid was measured using a fully automatic amino acid analyzer (JLC-500/V2 manufactured by JEOL, Ltd.) in a biological free amino acid analysis 110 min (high resolution) mode. The result is shown in FIG. 12. Each amino acid increased over time and, in particular, leucine and glutamic acid remarkably increased. Further, large amounts of tyrosine, phenylalanine, valine, and isoleucine were produced.

(2) Amino Acid Analysis of Milk Fermented by *Peniophora* sp.

Figure 13:
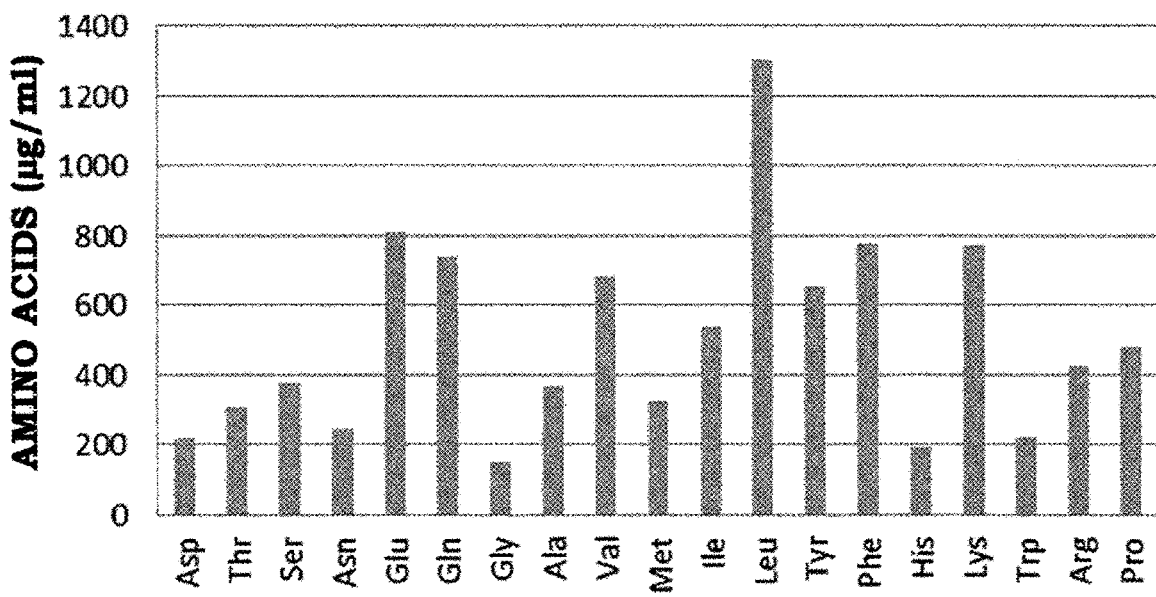
FIG. 13 is a graph showing a result of amino acid analysis of the fermented milk obtained using *Peniophora* sp.

The production amount of amino acid was measured in the *Peniophora* sp. fermented milk in the same manner as in above (1). The result is shown in FIG. 13. The result was similar to that of the *Neolentinus lepideus* fermented milk except that a relatively large amount of glutamine was produced.

It is known that glutamic acid has a taste exhibiting effect, an aromatic amino acid such as phenylalanine, tryptophan, and tyrosine has a tranquilizing effect, an anti-anxiety effect, and an analgesic effect, and a branched amino acid such as valine, leucine, and isoleucine has a recovery effect for muscle fatigue. Thus, the fermented milk of the present invention containing large amounts of these amino acids has such effects.

INDUSTRIAL APPLICABILITY

The present invention can be used in the fields of foods, medicines, and the like.

The invention claimed is:

1. A method for producing fermented milk having an angiotensin converting enzyme inhibitory activity, a hypotensive activity, and/or a stroke prevention activity, which comprises fermenting milk by culturing milk with a mushroom wherein the mushroom belongs to Gloeophyllaceae family, Polyporaceae family, or Corticiaceae family.

2. The method according to claim 1, wherein the mushroom is a mushroom belonging to Neolentinus genus, Trametes genus, or Peniophora genus.

3. The method according to claim 2, wherein the mushroom is a mushroom belonging to Neolentinus genus or Peniophora genus.

4. The method according to claim 1, wherein the milk is cow milk or skim milk.

5. Fermented milk having an angiotensin converting enzyme inhibitory activity, a hypotensive activity, and/or a stroke prevention activity, which is obtained by the method according to claim 1.

6. A method for producing a food or drink having an angiotensin converting enzyme inhibitory activity, a hypotensive activity, and/or a stroke prevention activity, which comprises including the fermented milk according to claim 5 in the food or drink.

7. A method for producing a pharmaceutical composition for angiotensin converting enzyme inhibition, hypotension, and/or stroke prevention, which comprises including the fermented milk according to claim 5 in the composition.

8. A method for producing Tyr-Pro, which comprises fermenting milk by culturing milk with a mushroom.

9. The method according to claim 8, wherein the mushroom is a mushroom belonging to Gloeophyllaceae family, Polyporaceae family, or Corticiaceae family.

10. The method according to claim 9, wherein the mushroom is a mushroom belonging to Neolentinus genus, Trametes genus, or Peniophora genus.

11. The method according to claim 10, wherein the mushroom is a mushroom belonging to Neolentinus genus or Peniophora genus.

12. The method according to claim 8, wherein the milk is cow milk or the skim milk.

* * * * *